United States Patent
Lostetter

(10) Patent No.: US 11,547,584 B2
(45) Date of Patent: Jan. 10, 2023

(54) DELIVERY SYSTEM AND METHOD TO RADIALLY CONSTRICT A STENT GRAFT

(71) Applicant: Bolton Medical, Inc., Sunrise, FL (US)

(72) Inventor: Timothy Lostetter, Sunrise, FL (US)

(73) Assignee: Bolton Medical, Inc., Sunrise, FL (US)

(*) Notice: Subject to any disclaimer, the term of this patent is extended or adjusted under 35 U.S.C. 154(b) by 279 days.

(21) Appl. No.: 16/379,354

(22) Filed: Apr. 9, 2019

(65) Prior Publication Data

US 2019/0231571 A1 Aug. 1, 2019

Related U.S. Application Data

(63) Continuation of application No. PCT/US2018/019349, filed on Feb. 23, 2018.
(Continued)

(51) Int. Cl.
*A61F 2/95* (2013.01)
*A61F 2/07* (2013.01)
(Continued)

(52) U.S. Cl.
CPC .................. *A61F 2/95* (2013.01); *A61F 2/07* (2013.01); *A61F 2/954* (2013.01); *A61F 2/9517* (2020.05);
(Continued)

(58) Field of Classification Search
CPC .... A61F 2/07; A61F 2/95; A61F 2/951; A61F 2/9517; A61F 2/954; A61F 2/962;
(Continued)

(56) References Cited

U.S. PATENT DOCUMENTS 4,787,391 A 11/1988 Elefteriades
5,123,917 A 6/1992 Lee
(Continued)

FOREIGN PATENT DOCUMENTS

CN 105832447 A 8/2016
EP 0786972 B1 1/2004
(Continued)

OTHER PUBLICATIONS

International Preliminary Report on Patentability for International Application No. PCT/US2018/019349 dated Aug. 27, 2019.
(Continued)

*Primary Examiner* — Kathleen S Holwerda
*Assistant Examiner* — Kankindi Rwego
(74) *Attorney, Agent, or Firm* — Foley Hoag LLP

(57) ABSTRACT

A delivery system includes a handle, a guidewire catheter, a nose cone at the distal end of the guidewire catheter that with the guidewire catheter defines an opening concentric with the guidewire catheter, a plurality of wires that extend distally from the handle and essentially parallel with and distributed radially about the guidewire catheter and a stent graft. The wires each extend between a portion of the stents and wall of the stent graft, whereby the stent graft is radially constrained until the wires are retracted. The delivery system can be employed in methods of treating arterial disease, such as aortic aneurysms.

3 Claims, 7 Drawing Sheets

Related U.S. Application Data

(60) Provisional application No. 62/463,043, filed on Feb. 24, 2017.

(51) Int. Cl.
    *A61F 2/954* (2013.01)
    *A61F 2/06* (2013.01)
    *A61M 25/09* (2006.01)

(52) U.S. Cl.
    CPC . *A61F 2002/061* (2013.01); *A61F 2002/9511* (2013.01); *A61F 2220/0075* (2013.01); *A61M 25/09041* (2013.01)

(58) Field of Classification Search
    CPC .......... A61F 2002/061; A61F 2002/072; A61F 2002/075; A61F 2002/077; A61F 2002/9511; A61F 2220/0075; A61M 25/09041
    USPC ...................................................... 623/1.11
    See application file for complete search history.

(56) References Cited

U.S. PATENT DOCUMENTS

| | | |
|---|---|---|
| 5,507,769 A | 4/1996 | Marin et al. |
| 5,755,769 A | 5/1998 | Richard et al. |
| 5,873,906 A | 2/1999 | Lau et al. |
| 6,113,623 A | 9/2000 | Sgro |
| 6,171,334 B1 | 1/2001 | Cox |
| 6,280,464 B1 | 8/2001 | Hayashi |
| 6,395,018 B1 | 5/2002 | Castaneda |
| 7,112,216 B2 | 9/2006 | Gregorich |
| 7,435,253 B1 | 10/2008 | Hartley et al. |
| 7,637,940 B2 | 12/2009 | Kocur et al. |
| 7,763,063 B2 | 7/2010 | Arbefeuille et al. |
| 8,007,605 B2 | 8/2011 | Arbefeuille et al. |
| 8,172,895 B2 | 5/2012 | Anderson et al. |
| 8,236,040 B2 | 8/2012 | Mayberry et al. |
| 8,277,501 B2 | 10/2012 | Chalekian et al. |
| 8,298,278 B2 | 10/2012 | Gregorich et al. |
| 8,333,800 B2 | 12/2012 | Sruszewski et al. |
| 8,343,211 B2 | 1/2013 | Gregorich et al. |
| 8,470,018 B2 | 6/2013 | Hartley et al. |
| 8,480,725 B2 | 7/2013 | Rasmussen et al. |
| 8,480,728 B2 | 7/2013 | Gregorich et al. |
| 8,486,129 B2 | 7/2013 | Lautherjung |
| 8,500,792 B2 | 8/2013 | Berra |
| 8,641,752 B1 | 2/2014 | Holm et al. |
| 8,808,351 B2 | 8/2014 | Osborne |
| 8,915,955 B2 | 12/2014 | West et al. |
| 8,926,693 B2 | 1/2015 | Duffy et al. |
| 9,101,455 B2 | 8/2015 | Roeder et al. |
| 9,101,506 B2 | 8/2015 | Arbefeuille et al. |
| 9,259,336 B2 | 2/2016 | Schaeffer et al. |
| 9,364,314 B2 | 6/2016 | Berra et al. |
| 9,375,308 B2 | 6/2016 | Norris |
| 9,439,751 B2 | 9/2016 | White et al. |
| 9,592,112 B2 | 3/2017 | Arbefeuille et al. |
| 9,827,123 B2 | 11/2017 | Arbefeuille et al. |
| 9,861,503 B2 | 1/2018 | Barthold et al. |
| 9,877,857 B2 | 1/2018 | Arbefeuille et al. |
| 9,913,743 B2 | 3/2018 | Arbefeuille et al. |
| 10,005,269 B2 | 6/2018 | Hall et al. |
| 10,080,674 B2 | 9/2018 | Yuan et al. |
| 10,265,202 B2 | 4/2019 | Greenberg et al. |
| 10,299,951 B2 | 5/2019 | Arbefeuille et al. |
| 10,390,930 B2 | 8/2019 | Arbefeuille et al. |
| 10,485,684 B2 | 11/2019 | Marmur et al. |
| 10,512,556 B2 | 12/2019 | Longo et al. |
| 10,617,542 B2 | 4/2020 | Chakfe et al. |
| 10,702,406 B2 | 7/2020 | Swift et al. |
| 10,898,357 B2 | 1/2021 | Arbefeuille et al. |
| 10,987,235 B2 | 4/2021 | Eubanks et al. |
| 11,000,359 B2 | 5/2021 | Torrance et al. |
| 11,219,540 B2 | 1/2022 | Arbefeuille |
| 11,278,390 B2 | 3/2022 | Lostetter |
| 11,291,572 B2 | 4/2022 | Garcia |
| 11,351,025 B2 | 6/2022 | Lostetter |
| 11,369,466 B2 | 6/2022 | Arbefeuille |
| 11,399,929 B2 | 8/2022 | Arbefeuille |
| 2002/0062133 A1 | 5/2002 | Gilson et al. |
| 2002/0177890 A1 | 11/2002 | Lenker |
| 2002/0188344 A1 | 12/2002 | Bolea et al. |
| 2002/0193872 A1 | 12/2002 | Trout et al. |
| 2004/0059406 A1 | 3/2004 | Cully et al. |
| 2004/0073289 A1* | 4/2004 | Hartley .................. A61F 2/95 623/1.13 |
| 2004/0138737 A1 | 7/2004 | Davidson et al. |
| 2005/0102021 A1 | 5/2005 | Osborne |
| 2005/0102023 A1 | 5/2005 | Yadin et al. |
| 2005/0131517 A1 | 6/2005 | Hartley et al. |
| 2005/0131518 A1 | 6/2005 | Hartley et al. |
| 2005/0131519 A1 | 6/2005 | Hartley |
| 2005/0131523 A1 | 6/2005 | Bashiri et al. |
| 2005/0154444 A1 | 7/2005 | Quadri |
| 2006/0015171 A1 | 1/2006 | Armstrong |
| 2006/0020319 A1 | 1/2006 | Kim et al. |
| 2006/0095118 A1 | 5/2006 | Hartley |
| 2006/0155359 A1 | 7/2006 | Watson |
| 2006/0184226 A1 | 8/2006 | Austin |
| 2007/0021822 A1 | 1/2007 | Boatman |
| 2007/0055358 A1 | 3/2007 | Krolik et al. |
| 2007/0055360 A1 | 3/2007 | Hanson et al. |
| 2007/0112418 A1 | 5/2007 | Eidenschink et al. |
| 2007/0135904 A1 | 6/2007 | Eidenschink et al. |
| 2007/0208414 A1 | 9/2007 | Sorenson et al. |
| 2007/0213805 A1 | 9/2007 | Schaeffer et al. |
| 2008/0091260 A1 | 4/2008 | Pomeranz et al. |
| 2008/0132988 A1 | 6/2008 | Jordan |
| 2008/0269867 A1 | 10/2008 | Johnson |
| 2009/0043377 A1 | 2/2009 | Greenberg et al. |
| 2009/0248135 A1 | 10/2009 | Bruszewski et al. |
| 2010/0004730 A1 | 1/2010 | Benjamin et al. |
| 2010/0234932 A1 | 9/2010 | Arbefeuille et al. |
| 2010/0268319 A1 | 10/2010 | Bruszewski et al. |
| 2010/0316830 A1 | 12/2010 | Hartley et al. |
| 2011/0077730 A1 | 3/2011 | Fenster |
| 2011/0190862 A1 | 8/2011 | Bashiri et al. |
| 2011/0257720 A1* | 10/2011 | Peterson .................... A61F 2/95 623/1.11 |
| 2012/0035714 A1 | 2/2012 | Duoke et al. |
| 2012/0191174 A1 | 7/2012 | Vinluan et al. |
| 2012/0221096 A1 | 8/2012 | Roeder et al. |
| 2012/0271401 A1* | 10/2012 | Bruszewski ............ A61F 2/966 623/1.35 |
| 2013/0116773 A1 | 5/2013 | Roeder et al. |
| 2013/0116775 A1 | 5/2013 | Roeder et al. |
| 2013/0123900 A1 | 5/2013 | Eblacas et al. |
| 2013/0158648 A1 | 6/2013 | Hartley et al. |
| 2013/0184806 A1 | 7/2013 | Arbefeuille et al. |
| 2013/0282102 A1 | 10/2013 | Peterson |
| 2013/0289696 A1 | 10/2013 | Maggard et al. |
| 2013/0289713 A1 | 10/2013 | Pearson et al. |
| 2014/0039597 A9 | 2/2014 | Arbefeuille et al. |
| 2014/0046428 A1 | 2/2014 | Cragg et al. |
| 2015/0105819 A1 | 4/2015 | Becking et al. |
| 2015/0105849 A1 | 4/2015 | Cohen et al. |
| 2015/0202065 A1* | 7/2015 | Shalev .................... A61F 2/93 623/1.2 |
| 2015/0202067 A1 | 7/2015 | Barrand et al. |
| 2015/0272755 A1 | 10/2015 | Arbefeuille et al. |
| 2015/0335452 A1* | 11/2015 | Rao .................... A61F 2/2427 623/23.66 |
| 2016/0106564 A1 | 4/2016 | Roeder et al. |
| 2016/0184078 A1 | 6/2016 | Choubey et al. |
| 2016/0199207 A1 | 7/2016 | Treacy et al. |
| 2016/0296353 A1 | 10/2016 | Skender |
| 2016/0302950 A1* | 10/2016 | Marmur ................ A61F 2/966 |
| 2017/0135807 A1 | 5/2017 | Arbefeuille et al. |
| 2017/0281382 A1 | 10/2017 | Lostetter et al. |
| 2018/0071123 A1 | 3/2018 | Arbefeuille et al. |
| 2019/0350694 A1 | 11/2019 | Arbefeuille et al. |
| 2020/0352700 A1 | 11/2020 | Torrance et al. |

(56) References Cited

U.S. PATENT DOCUMENTS

| | | |
|---|---|---|
| 2021/0100669 A1 | 4/2021 | Arbefeuille et al. |
| 2022/0087841 A1 | 3/2022 | Arbefeuille |
| 2022/0168091 A1 | 6/2022 | Lostetter |

FOREIGN PATENT DOCUMENTS

| | | |
|---|---|---|
| EP | 1847234 A1 | 10/2007 |
| EP | 1847236 A2 | 10/2007 |
| EP | 2471498 A1 | 7/2012 |
| EP | 2517672 A1 | 10/2012 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 2606851 B1 | 11/2015 |
| EP | 3040054 A1 | 7/2016 |
| EP | 3068339 A1 | 9/2016 |
| EP | 3146993 A1 | 3/2017 |
| EP | 3272319 A1 | 1/2018 |
| FR | 2932979 A1 | 1/2010 |
| GB | 2464978 A | 5/2010 |
| JP | 2012/152549 A | 8/2012 |
| WO | WO-97/03624 A1 | 2/1997 |
| WO | WO-99/29262 A1 | 6/1999 |
| WO | WO-01/60285 A1 | 8/2001 |
| WO | WO-02/083038 A2 | 10/2002 |
| WO | WO-03/099108 A2 | 12/2003 |
| WO | WO-2005/034809 A1 | 4/2005 |
| WO | WO-2006/037086 A1 | 4/2006 |
| WO | WO-2009/148594 A1 | 12/2009 |
| WO | WO-2010/024880 A1 | 3/2010 |
| WO | WO-2010/030370 A1 | 3/2010 |
| WO | WO-2010/127040 A1 | 11/2010 |
| WO | WO-2012/116368 A2 | 8/2012 |
| WO | WO-2012/145823 A1 | 11/2012 |
| WO | WO-2014/149022 A1 | 9/2014 |
| WO | WO-2015/070792 A1 | 5/2015 |
| WO | WO-2016/122862 A1 | 8/2016 |
| WO | WO-2017/218474 A1 | 12/2017 |
| WO | WO-2018/026768 A1 | 2/2018 |

OTHER PUBLICATIONS

International Search Report and Written Opinion for International Application No. PCT/US2018/019349 dated May 3, 2018.

Wang et al. "Preliminary experimental study on a novel adjustable sutureless aortic prosthesis" Chinese Journal of Experimental Surgery, 23(11): 1325-1327 w/ English Abstract (2006).

* cited by examiner

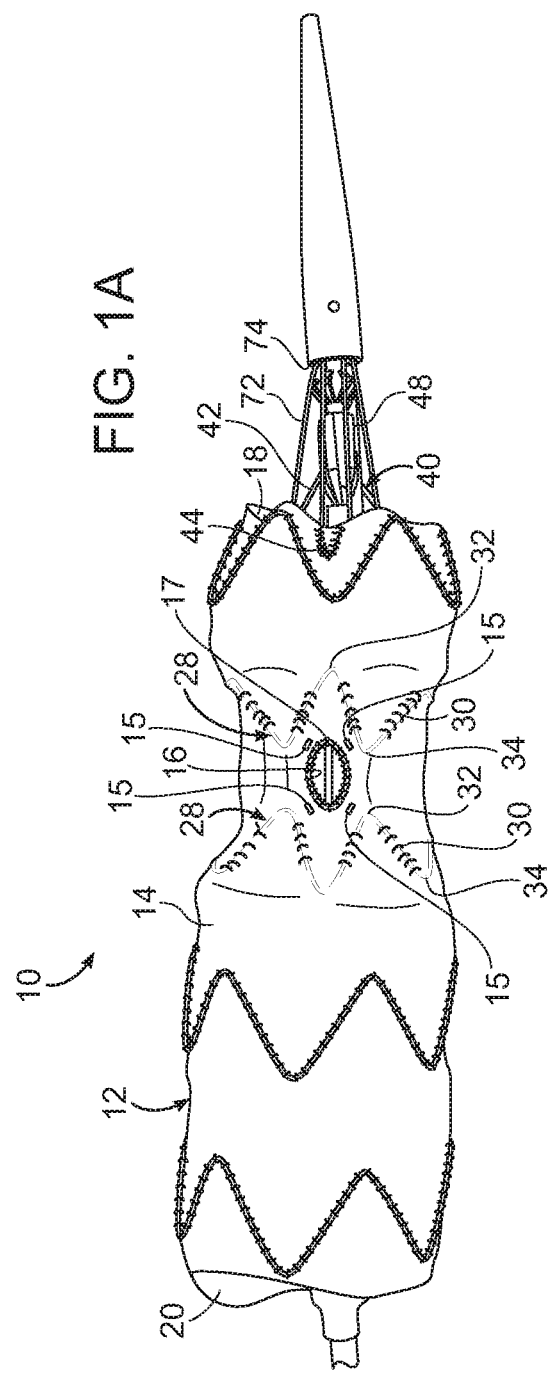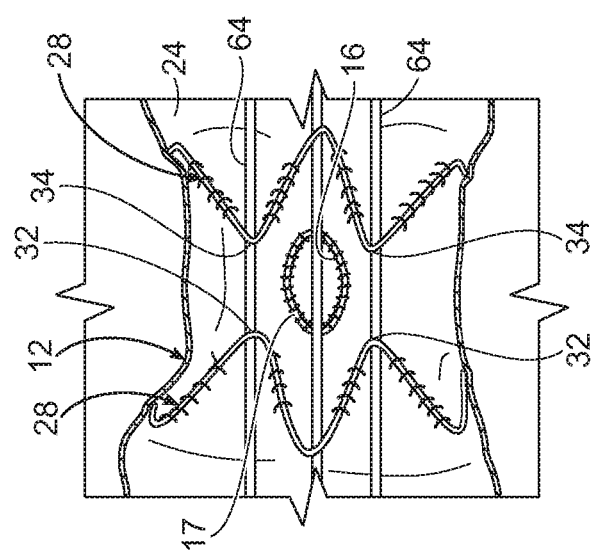

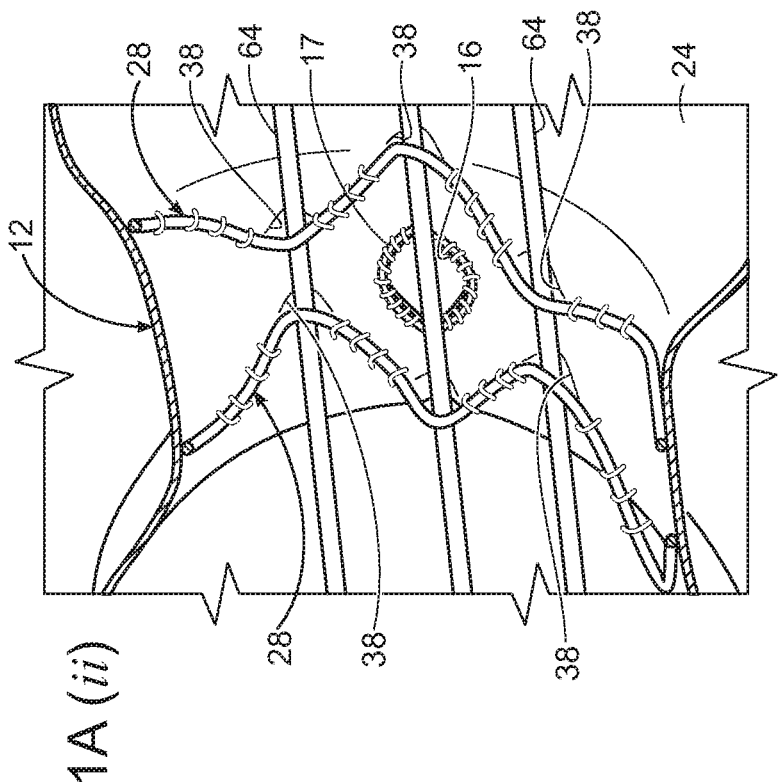
FIG. 1A(ii)
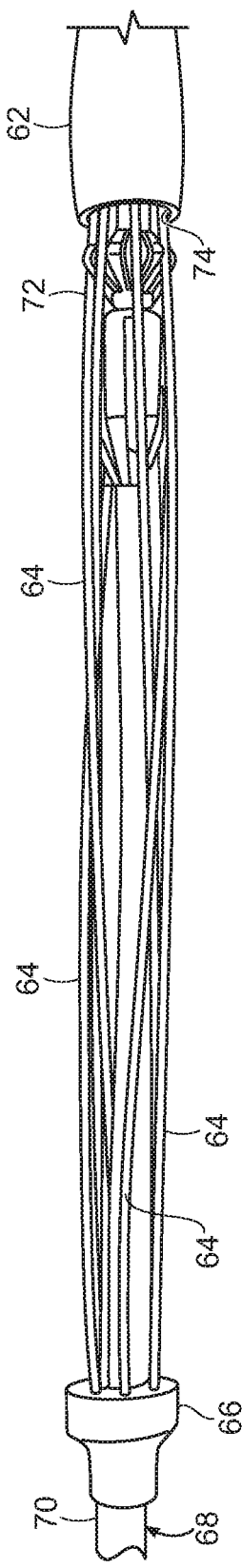
FIG. 1A(iii)

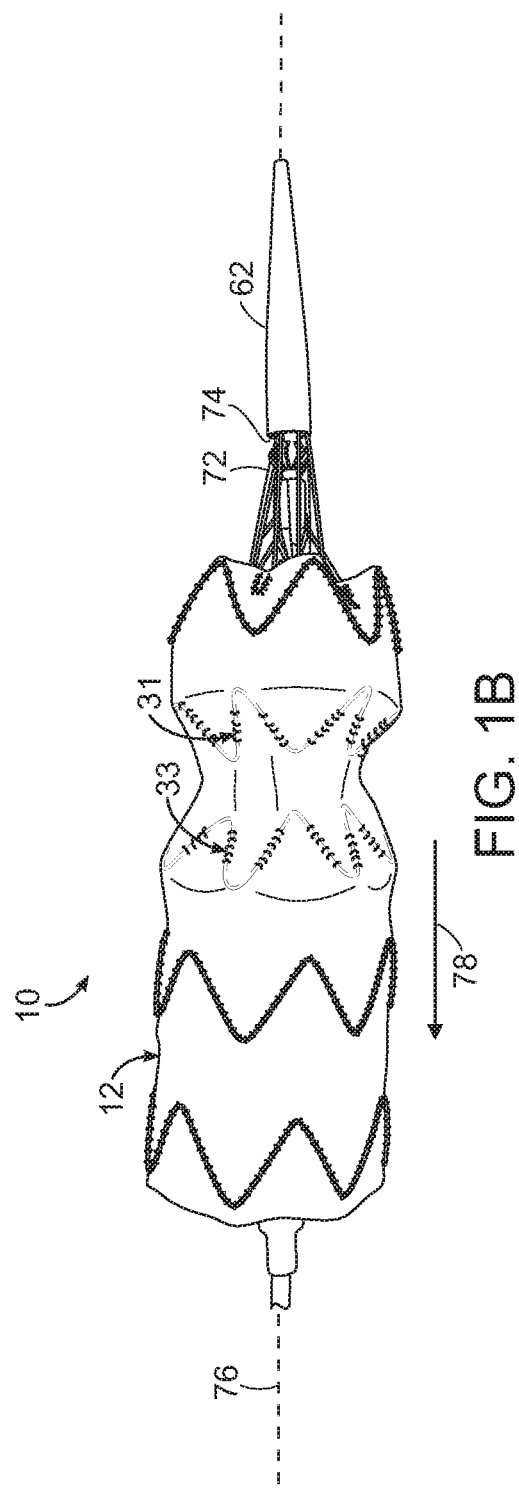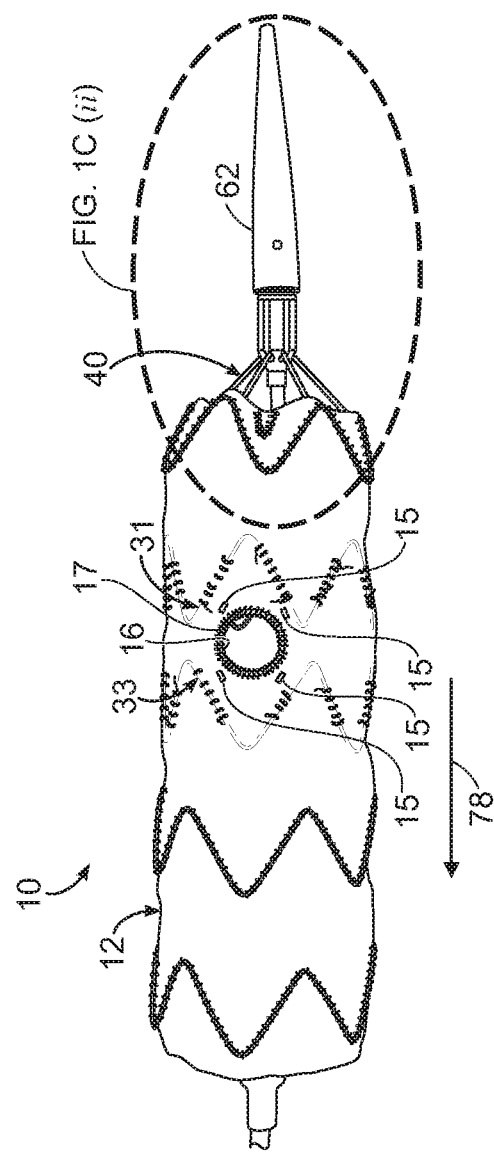

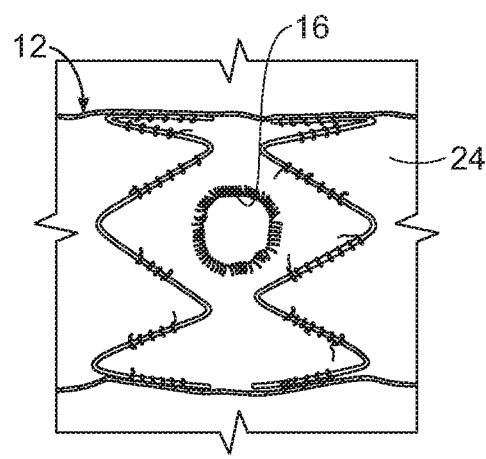
FIG. 1C (i)
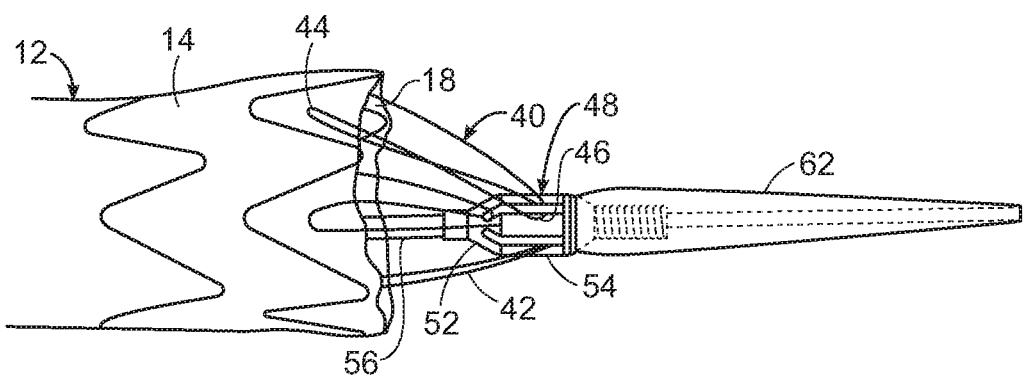
FIG. 1C (ii)
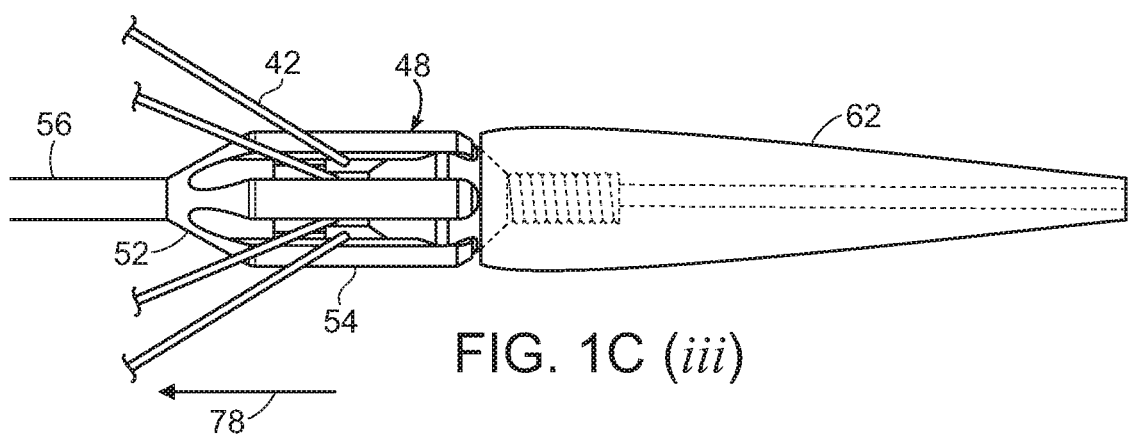
FIG. 1C (iii)

FIG. 1C (iv)

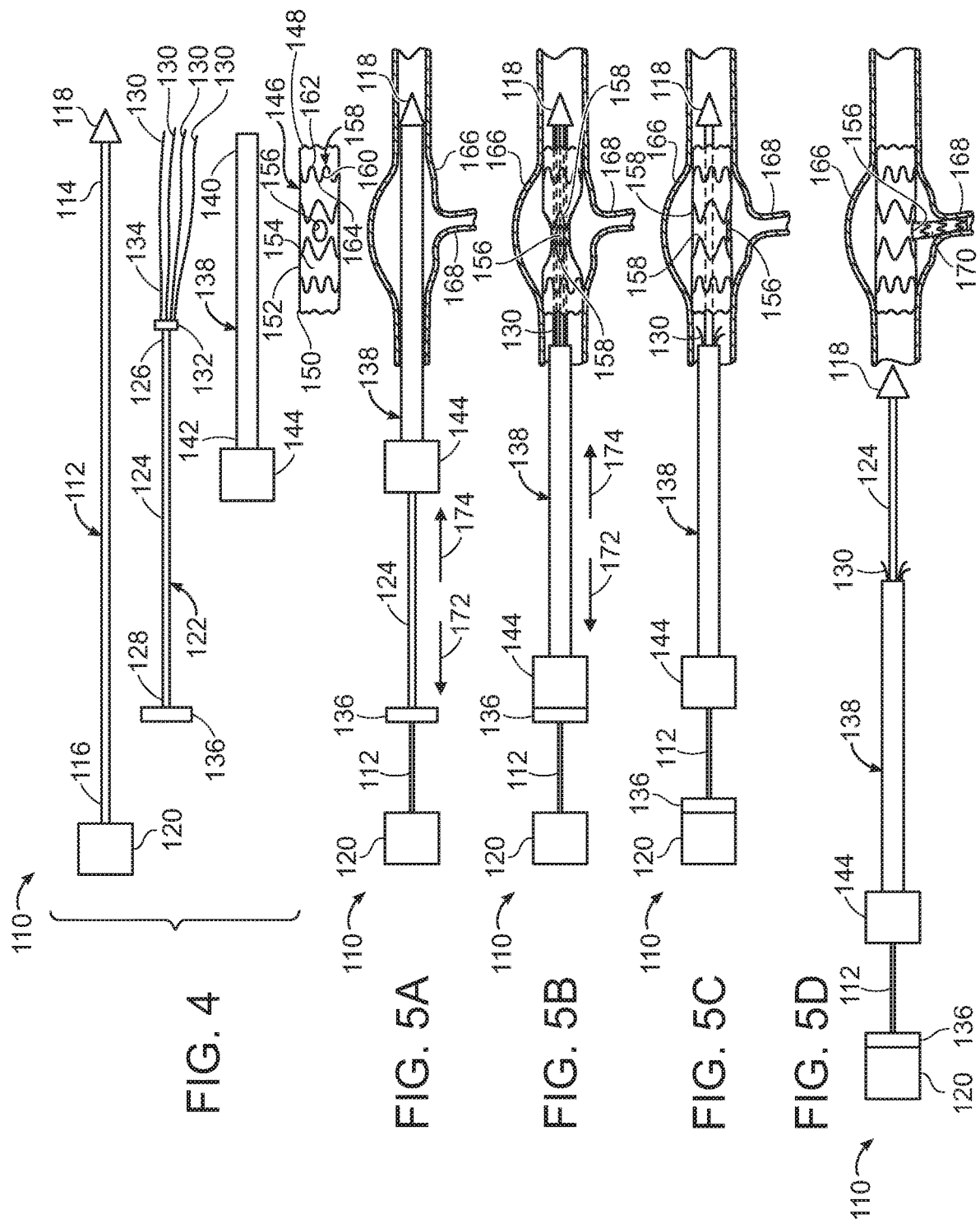

DELIVERY SYSTEM AND METHOD TO RADIALLY CONSTRICT A STENT GRAFT

RELATED APPLICATION

This application is a continuation of International Application No. PCT/US2018/019349, which designated the United States and was filed on Feb. 23, 2018, published in English, which claims the benefit of U.S. Provisional Application No. 62/463,043, filed on Feb. 24, 2017. The entire teachings of the above applications are incorporated herein by reference.

BACKGROUND

Fenestrated endovascular aortic repair (FEVAR) is a minimally invasive procedure to treat aortic aneurysms that span blood vessels arising from the aorta that supply blood to vital organs including the kidneys, intestine and liver. Endovascular grafts employed in FEVAR define fenestrations for insertion of branch prostheses that serve as passageways for blood flow through arterial branches to vital organs following implantation of the endovascular graft. Maximizing blood flow to vital organs and minimizing endoleaks following repair of aneurysms with fenestrated vascular prostheses, such as juxtarenal aortic aneurysms and short-neck abdominal aortic aneurysms, present medical challenges that must be overcome if additional surgical intervention is to be avoided.

Therefore, a need exits for new and improved delivery devices, endovascular repair devices for implanting stent grafts, and for methods of their use, to treat aortic pathologies, in particular aortic aneurysms, such as juxtarenal and short-neck abdominal aortic aneurysms.

SUMMARY

The present invention relates to stent graft delivery systems and methods for their use in treating and repairing aortic vascular damage, such as vascular damage associated with aortic aneurysms, including aortic aneurysms in regions of the aorta having arterial branches that supply blood to vital organs and tissues, such as thoracic aortic aneurysms, abdominal aortic aneurysms, thoracoabdominal aortic aneurysms, juxtarenal aortic aneurysms and short-neck abdominal aortic aneurysms.

In one embodiment, the invention is a delivery system that includes a stent graft and a plurality of wires extending through a lumen of the stent graft. The stent graft includes a luminal graft component defining a fenestration and having a proximal open end, a distal open end, an outside surface and an inside surface, the inside surface defining a lumen extending from the proximal open to the distal open end. A plurality of radially self-expanding stents is distributed longitudinally along and fixed to the luminal graft component proximally and distally to the fenestration. At least one of the luminal graft component and at least a portion of the radially self-expanding stents define, separately or in combination, openings within the lumen that are distributed about the fenestration. The plurality of wires extend longitudinally through the lumen of the luminal graft component and at least one of the proximal end and the distal end of the luminal graft component. At least one wire on each lateral side of the fenestration extends longitudinally through the at least one opening, whereby the stent graft is radially constricted by the wires.

In another embodiment, the invention is a delivery system that includes a stent graft having a luminal graft component defining a fenestration and having a proximal open end, a distal open end, an outside surface and an inside surface, the inside surface defining a lumen extending from the proximal open end to the distal open end. A plurality of stents of the stent graft are distributed longitudinally along and are fixed to the luminal graft component proximally and distally to the fenestration, the stents including struts that define proximal and distal apices, and wherein the fenestration is radially between bare apices of the stents. A plurality of wires extends longitudinally through the lumen of the luminal graft component and at least one of the proximal open end and the distal open end, where at least one wire on each lateral side of the fenestration extends between longitudinally aligned bare apices on each respective lateral side of the fenestration, whereby the stent graft is radially constricted at the fenestration by the wires.

In yet another embodiment, the invention is a delivery system that includes a handle, a guidewire catheter, a nose cone, a plurality of wires and a stent graft. The guidewire catheter extends distally from the handle and has a distal end. The nose cone is at the distal end of the guidewire catheter, and defines an opening in line or concentric with the guidewire catheter. The stent graft has a proximal open end near the nose cone, a distal open end, and a wall extending between the proximal open end and the distal open end, the wall defining a lumen through which the guidewire catheter extends, and a plurality of radial stents distributed longitudinally along the wall and wherein at least one of the wall and radial stents define, separately or in combination, openings within the lumen and distributed about the fenestration. A plurality of wires each extend distally from the handle and longitudinally through the lumen and at least one of the proximal open end and the distal open end, at least one wire on each lateral side of the fenestration. The plurality of wires extend between at least a portion of the stents and the wall, whereby the stent graft is radially constricted until the wires are retracted from the at least one opening.

In a further embodiment, the invention is a method for delivering a fenestrated stent graft to an aneurysm site of a patient, wherein the aneurysm site spans a portion of an artery that includes an arterial branch, and includes directing a delivery system to an aneurysm site of the patient. The delivery system includes a stent graft, having a luminal graft component defining a fenestration and having a proximal open end, a distal open end, an outside surface and an inside surface, wherein the inside surface defining a lumen extending from the proximal open end to the distal open end. A plurality of stents is distributed longitudinally along and fixed to the luminal graft component proximally and distally to the fenestration. At least one of the luminal graft component and at least a portion of the radially self-expanding stents define, separately or in combination, openings within the lumen and are distributed about the fenestration. The stent graft of the delivery system employed by the method of the invention further includes a plurality of wires extending longitudinally through the lumen of the luminal graft component and at least one of the proximal open end and distal open end, at least one wire on each lateral side of the fenestration extending longitudinally through the at least one opening, whereby the stent graft is radially constricted by the wires. The fenestration of the stent graft is then aligned with a proximal end of the arterial branch, and the wires are retracted to release the constricted portion of the stent graft spanning the fenestration, whereby the fenestration is proximate to the proximal end of the arterial branch, thereby delivering the fenestrated stent graft to the aneurysm site of the patient.

This invention has many advantages. For example, the physician can selectively constrict the radial dimension of a partially deployed stent graft at the fenestration, thereby enabling the physician to more accurately and safely rotate or otherwise reposition the stent graft to align the fenestration with an arterial branch, thereby providing improved accuracy for alignment of the fenestration over delivery systems that are only able to position a fenestration of a stent graft prior to deployment. As a consequence, a stent graft can be deployed at a surgical site with more accuracy, less risk of injury to the vasculature of the subject, and without significant risk of distorting the intended shape of the stent graft when implanted at the surgical site and following delivery of a branch prosthesis through the fenestration and into an arterial branch.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1A is a side view of one embodiment of a delivery device of the invention showing wires radially constricting a stent graft prosthesis at a fenestration prior to delivery of the stent graft prosthesis at an aneurysm site of a patient.

FIG. 1A(i) is a detail of the fenestration, as shown in FIG. 1A, but viewed from within a lumen defined by the stent graft.

FIG. 1A(ii) is a detail of the fenestration and plurality of wires viewed from within a lumen defined by the stent graft, as shown in FIG. 1A(i), wherein at least one of the luminal graft component and at least a portion of the radially self-expanding stents define, in combination, openings within the lumen and distributed about the fenestration.

FIG. 1A(iii) is a side view of a portion of the delivery system of the invention that includes a plurality of wires.

FIG. 1B is a side view of the embodiment shown in FIG. 1A, but rotated 180° on its longitudinal axis.

FIG. 1C is a side view of the embodiment shown in FIGS. 1A and 1B, but following retraction of the wires radially constricting the stent graft at the fenestration.

FIG. 1C(i) is a detail of the fenestration as shown in FIG. 1C but viewed from within the lumen defined by the stent graft.

FIG. 1C(ii) is a detail of proximal apices of the bare stent of the embodiment shown in FIG. 1C in a captured state at the apex capture device.

FIG. 1C(iii) is a side view of the proximal end of the delivery device of FIG. 1C showing capture of proximal apices of the bare stent within opening defined by distal and proximal components of the apex capture device.

FIG. 1C(iv) is a detail of the apex capture assembly shown in FIGS. 1C(ii) and 1C(iii) following release of the proximal apices of the bare stent by retraction of the proximal apex capture component from the distal apex capture component of the apex capture assembly.

FIG. 4 is an exploded view of one embodiment of a delivery system of the invention.

FIG. 5A is an assembled view of the embodiment of the delivery system of the invention shown in FIG. 4 when assembled, and containing a stent graft (not shown) loaded within an introducer sheath of the delivery device.

FIG. 5B is a side view of the embodiment shown in FIG. 5A, following retraction of an introducer sheath to thereby expose a stent graft constricted at a fenestration by wires running through a luminal graft component of the stent graft.

FIG. 5C is a side view of the embodiment shown in FIGS. 5A and 5B, following retraction of the wires radially constricting the stent graft at the fenestration.

FIG. 5D is a side view of the delivery system of FIGS. 5A through 5C, following retraction of portions of the delivery system not associated with the stent graft after delivery of a branch prosthesis through the fenestration and into an arterial branch of the aneurysm, thereby treating the aneurysm.

DETAILED DESCRIPTION

The invention is generally directed to delivery systems for use in treating and repairing aortic vascular damage, such as vascular damage associated with an aortic aneurysm in regions of the aorta having arterial branches to vital organs and tissues, including thoracic aortic aneurysms, abdominal aorta aneurysms, thoracoabdominal aortic aneurysms, juxtarenal aortic aneurysms and short-neck abdominal aortic aneurysms.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments of the invention follows.

When reference is made herein to a prosthesis, also referred to herein as "stent graft," "stent graft prosthesis," or "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient. A "longitudinal axis," as that term is defined herein, means an axis along a lengthwise direction of a body that also passes through a center of gravity of the body.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

Figure 1D:
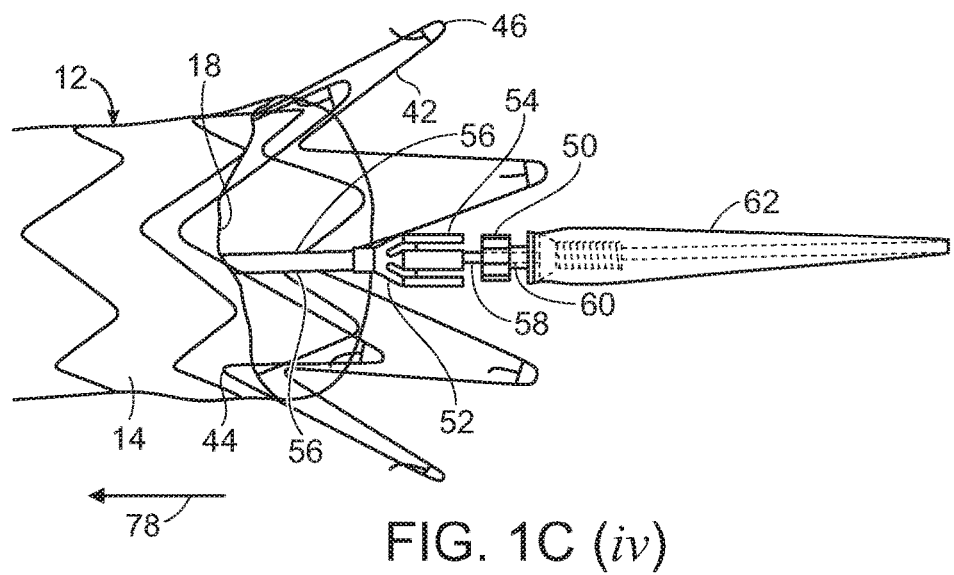
FIG. 1D is a side view of another embodiment of the delivery device of FIGS. 1A-1C, following retraction of the wires constricting the stent graft prosthesis and release of the proximal apices of a bare stent that includes barbs extending distally from a bridge that spans adjacent to struts to define an eyelet.
Figure 1D:
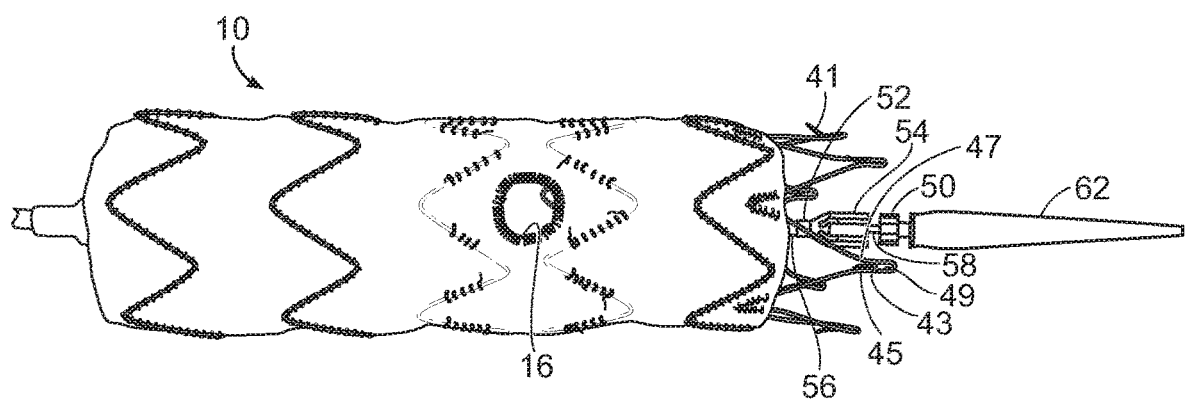

One embodiment of a delivery system of the invention is shown in FIGS. 1A through 1D. As can be seen in FIG. 1A, delivery system 10 includes stent graft 12. Stent graft 12 includes luminal graft component 14 defining fenestration 16. Luminal graft component 14 includes proximal open end 18, distal open end 20, outside surface 22 and inside surface 24. Inside surface 24 defines lumen 26 extending from proximal open end 18 to distal open end 20. Luminal graft component 14 is formed of a suitable material, such as is known in the art. Examples of suitable materials of luminal graft component include at least one member selected from the group consisting of polytetrafluoroethylene (PTFE), such as expanded PTFE (ePTFE), and polyethylene terephthalate (PET), such as woven polyester.

A plurality of stents 28 are distributed longitudinally along and are fixed to luminal graft component 14 proximally and distally to fenestration 16. Stents 28 include struts 30, that join to define proximal apices 32 and distal apices 34. FIGS. 1A(i) and 1A(ii) are detail views of a portion of stent graft 12 shown from within lumen 26 and, specifically, of fenestration 16 viewed from inside lumen 26. As can be seen therein, fenestration 16 is defined by luminal graft component 14 between bare proximal apices 32 and bare distal apices 34, collectively referred to as bare apices 36, of radially self-expanding stents 28.

As shown in FIGS. 1A and 1C, fenestration 16 is nested between struts 30 of immediately proximal stent 31 and immediately distal stent 33. In another embodiment, not shown, fenestration 16 can be between a distal apex of an immediately proximal stent and proximal to a proximal apex of an immediately distal stent. Other arrangements of fenestration 16 and immediately proximal stent 31 and distal stent 33 are also suitable.

As can be seen in FIG. 1A(ii), openings 38 are defined by bare apices 36 of stent 28 and luminal graft component 14. Openings 38 are distributed about fenestration 16. In this embodiment, at least one wire 64 traverses fenestration 16.

Stents 28 are formed of a suitable material, such as is known in the art, for example, stainless steel, and shape memory alloys, such as nitinol. Shape memory alloys can be employed to form radially self-expanding stents. Where stents are not radially self-expanding, they can be expanded in a radial direction by, for example, employing a balloon catheter, as is known in the art. Optionally, stents 28 can include a radiopaque component. Alternatively, radiopaque markers 15, such as those known in the art, are secured, such as by suturing or employing a biocompatible adhesive, to luminal graft component 14 and about the periphery of fenestration 16. In an embodiment, ring 17 is secured to a perimeter of fenestration 16, such as by sutures or biocompatible adhesive. In another embodiment, at least one ring 17, stents and radiopaque markers 15 include radiopaque material, such as at least one radiopacifier selected from the group consisting of barium sulfate, bismuth, tungsten, platinum, platinum-iridium, tantalum and tantalum-tungsten.

It is to be understood that, in an alternative embodiment, only one opening 38, at either a proximal apex 32 or distal apex 34 is required on each lateral side of fenestration 16. Further, in another embodiment, while a plurality of openings are defined on each side of fenestration, the apices at each opening 38 can both be proximal apices or distal apices or a combination of proximal apices 32 and distal apices 34 of stents 28. In still another embodiment, openings 38 are defined by immediately proximal and distal stents 28 that are proximal and distal to fenestration 16, either in addition to openings 38 or instead of being on both lateral sides of fenestration 16.

As can be seen in FIG. 1A(iii), plurality of wires 64 extend longitudinally through lumen 26 of luminal graft component 14 and through proximal open end 18 and distal open end 20. Wires 64 extend distally from buttress 66 which, in turn, is fixed to wire catheter 68 at proximal end 70. Distal ends 72 of wires 64 are releasably fixed within cavity 74 defined by nose cone 62. Returning to FIGS. 1A(i) and 1A(ii), wires 64 extend through openings 38, whereby stent graft 12 is radially constricted by wires 64. Fenestration 16, about which openings 38 are distributed, is also constricted by wires 64 passing through openings 38 about fenestration 16. FIG. 1B is a side view of stent graft delivery system 10 shown in FIG. 1A, but rotated 180° about its longitudinal axis 76. Wires 64 are formed of suitable material, such as is known in the art, for example, stainless steel, or a shape memory alloy, such as nitinol.

As shown in the transition from FIGS. 1A and 1B to FIG. 1C, retraction of wires 64 in a proximal direction indicated by arrow 78 releases distal ends 72 of wires 64 from concentric cavity 74 at nose cone 62 and through openings 38 of immediately-proximal stent 31 and immediately-distal stent 33. Retraction of wires 64 from openings 38 in the direction of arrow 78 releases immediately proximal stent 31 and immediately distal stent 33 and, therefore, fenestration 16 from constriction, thereby causing stents 31,33 and luminal graft component 14 to radially expand to assume an expanded shape, shown in FIG. 1C.

As can been seen in FIG. 1C(ii) through 1C(iv), stent graft 12 optionally includes bare stent 40 at proximal open end 18. Bare stent 40 includes struts 42 that join at opposite ends to define distal apices 44 that are fixed to luminal graft component 14 at proximal open end 18, and proximal apices 46 (FIG. 1C(iv)) that are captured at apex capture assembly 48. Apex capture assembly 48 includes distal apex capture portion 50 and proximal apex capture portion 52 having tines 54. Tines 54 extend between struts 42 of bare stent 40 and are in mating relation with distal apex capture portion 50 to thereby capture proximal apices 46 of bare stent 40. Apex capture catheter 56 extends proximally from proximal apex capture portion 52 and through lumen 26 of stent graft 12. Guidewire catheter 58 extends through apex capture catheter 56 and includes distal end 60. Nose cone 62 is fixed to distal end 60 of guidewire catheter 58.

Retraction of proximal apex capture portion 52 in a proximal direction along guidewire catheter 58 indicated by arrow 78 causes separation of proximal apex capture portion 52 from distal apex capture portion 50, thereby freeing proximal apices 46 of bare stent 40 and allowing radial expansion of bare stent 40, as shown in detail in FIG. 1C(iv). Stent graft 12 is thereby released from stent graft delivery device 10, as shown in FIG. 1D. In an embodiment, radially expanded bare stent 40 includes a fixation device, such as barbs 41, that extend distally from bridge 43 that spans adjacent struts 45,47 to define eyelet 49.

Figure 2:
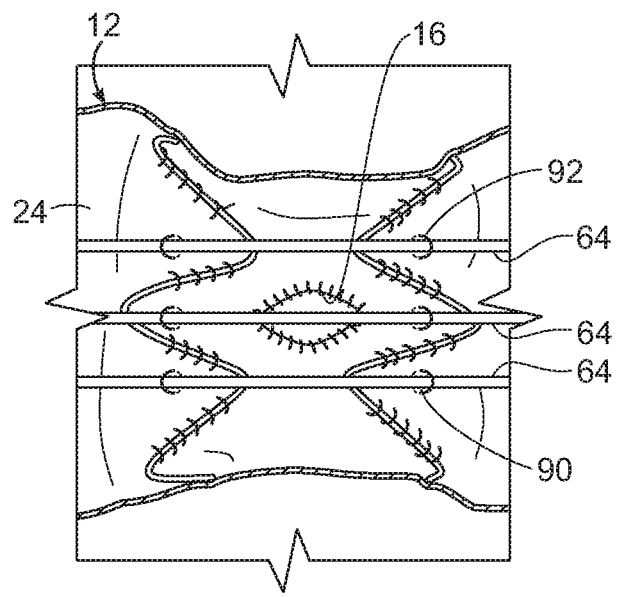
FIG. 2 is a detail of another embodiment of a portion of a delivery device of the invention viewed from within a lumen defined by a stent graft at a fenestration in the stent graft.
Figure 3:
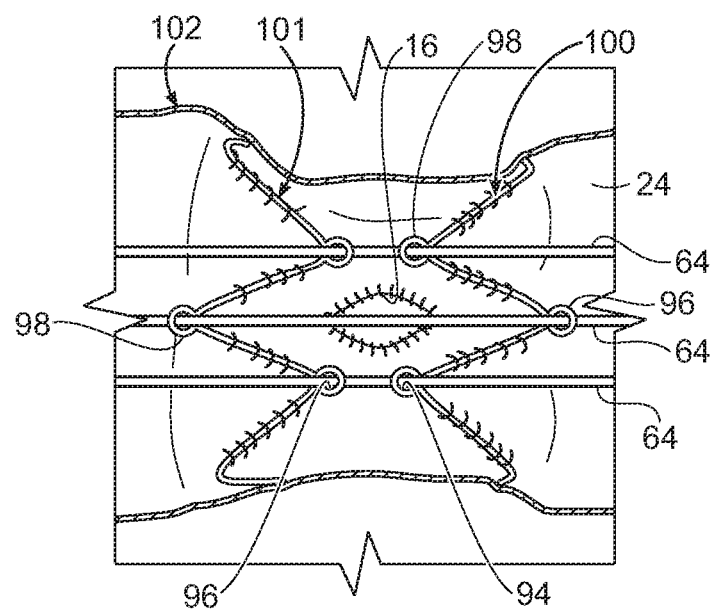
FIG. 3 is a detail of still another embodiment of a portion of a delivery device of the invention viewed from within a lumen defined by a stent graft at a fenestration in the stent graft.

In another embodiment, shown in FIG. 2, openings 90 through which wires 64 extend are defined by ligature loops 92 within luminal graft component 14. In yet another embodiment, shown in FIG. 3, openings 94 through which wires 64 extend are defined by at least one of proximal apices 96 and distal apices 98 of stents 100,101 of stent graft prosthesis 102.

FIG. 4 is an exploded view of component parts of another embodiment of a delivery system of the invention. As shown therein, delivery system 110 includes guidewire catheter 112, having distal end 114 and proximal end 116. Nose cone 118 is fixed to distal end 114, while proximal handle 120 is fixed to proximal end 116 of guidewire catheter 112. Wire component 122 includes wire catheter 124 having distal end 126 and proximal end 128. Plurality of wires 130 extend distally from distal end 126 of wire catheter 124. Optionally, buttress 132 links distal end 126 of wire catheter 124 to proximal ends 134 of wires 130. Wire catheter handle 136 is fixed to proximal end 128 of wire catheter 124. Introducer sheath 138 includes distal end 140 and proximal end 142. Distal handle 144 is fixed to proximal end 142 of introducer sheath 138. Stent graft 146 includes proximal end 148 and distal end 150. Luminal graft component 152 has outside surface 154 and defines fenestration 156. Stents 158 are distributed longitudinally along luminal graft component 152 and include struts 160 that define proximal apices 162 and distal apices 164.

FIG. 5A is a side view of delivery system 110 of FIG. 4 in assembled form. As shown therein, wire catheter 124 and wire catheter handle 136 are disposed about guidewire catheter 112. Introducer sheath 138 and distal handle 144 are disposed about wire catheter 124 and wires 130, and about guidewire catheter 112. Stent graft 146, not shown, is radially constricted and loaded within introducer sheath 138. In a method of the invention, stent graft delivery system 110 and, specifically, introducer sheath 138 and nose cone 118 are directed to aneurysm site 166 of a patient. Aneurysm site 166, includes arterial branch 168. Thereafter, distal handle 144 is retracted in a proximal direction indicated by arrow 172 toward the surgeon, thereby exposing stent graft prosthesis at aneurysm site 166 as can be seen in FIG. 5B. Fenestration 156 and stents 158, immediately proximal and distal to fenestration 156, are radially constricted by wires 130 extending through openings (not shown) within stent graft 146 that are distributed about fenestration 156. It is to be understood that, in an alternative embodiment (not shown), wherein stent graft 146 is further constricted, such as by an inner sheath extending about stent graft, but within introducer sheath 138, stent graft 146 can be advanced to aneurysm site 166 by advancing proximal handle 120 in a distal direction indicated by arrow 174 toward distal handle 144. Independent constricting device (not shown) can then be removed to thereby partially release stent graft 146 from radial constriction. Stent graft 146, however, would remain radially constricted at stents 158 immediately distal and proximal to fenestration 156 by wires 130.

As can be seen in the transition from FIGS. 5B to FIG. 5C, stent graft 146 is then longitudinally and axially aligned so that fenestration 156 is substantially aligned with arterial branch 168 of aneurysm 166. Wire catheter 136 handle is then retracted in a proximal direction in the direction of arrow 172 toward the surgeon, thereby retracting wires 130 from openings (not shown) at stents 158 immediately proximal and distal to fenestration 156, thereby causing stents 158 and fenestration 156 to expand to the position shown in FIG. 5C. As shown in the transition from FIG. 5C to FIG. 5D, guidewire catheter 112 and nose cone 118 are then retracted with the remainder delivery device 110 from stent graft prosthesis 146, and branch prosthesis 170 can be delivered through fenestration 156 to arterial branch 168 by a suitable method, such as is known in the art, thereby treating aortic aneurysm 166 of the patient.

Vascular prostheses implanted by the stent graft systems and methods of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branch of major blood vessels, including peripheral blood vessels.

The teachings of all patents, published applications and references cited herein are incorporated by reference in their entirety. The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712, 9,827,123, 9,877,857, 9,907,686; U.S. patent application Ser. Nos. 14/575,673; 15/166,818; 15/167,055; 14/272,818; 14/861,479; 15/478,424; 15/478, 737; 15/587,664; 15/604,032; 15/672,404; 15/816,772; 15/839,272; 15/417,467; PCT/US2017/025844; PCT/US2017/025849; PCT/U52017/025912; PCT/US2017/034223 and PCT/US2017/046062, are also incorporated by reference in their entirety.

The relevant teachings of International Patent Applications Nos.: PCT/US2018/019355; PCT/US2018/019344; PCT/US2018/019353; PCT/US2018/019354; PCT/US2018/019352; PCT/US2018/019342; PCT/US2018/019350; PCT/US2018/019356; PCT/US2018/019351; and PCT/US2018/019510, are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:
1. A delivery system, comprising:
   a) a stent graft including
      i) a luminal graft component defining a fenestration and having a proximal open end, a distal open end, an outside surface and an inside surface, the inside surface defining a lumen extending from the proximal open end to the distal open end, and
      ii) a plurality of radially self-expanding stents distributed longitudinally along and fixed to the luminal graft component proximally and distally to the fenestration, and
      iii) a plurality of ligature loops within the lumen; and
   b) a plurality of wires extending longitudinally through the lumen of the luminal graft component and at least one of the proximal open end and the distal open end, at least one of the plurality of wires on each lateral side of the fenestration extending longitudinally through at least a portion of the plurality of ligature loops, whereby the stent graft is radially constricted by the plurality of wires.
2. A delivery system, comprising:
   a) a stent graft including
      i) a luminal graft component defining a fenestration and having a proximal open end, a distal open end, an outside surface and an inside surface, the inside surface defining a lumen extending from the proximal open end to the distal open end, and
  ii) a plurality of radially self-expanding stents distributed longitudinally along and fixed to the luminal graft component proximally and distally to the fenestration, wherein the plurality of stents are radially self-expandable and include struts that define proximal and distal apices, wherein at least a portion of the proximal apices of the most proximal stent of the stent graft are bare, and wherein at least one of the luminal graft component and at least a portion of the plurality of radially self-expanding stents of the stent graft define, separately or in combination, openings within the lumen and distributed about the fenestration of the luminal graft component of the stent graft;
b) a plurality of wires extending longitudinally through the lumen of the luminal graft component and at least one of the proximal open end and the distal open end, at least one of the plurality of wires on each lateral side of the fenestration extending longitudinally through at least one of the openings, whereby the stent graft is radially constricted by the plurality of wires;
c) a guidewire catheter having a proximal end and a distal end, and extending through the lumen;
d) a nose cone fixed to the distal end of the guidewire catheter and defining at least in part an opening that releasably retains distal ends of the plurality of wires;
e) a proximal handle fixed to the proximal end of the guidewire catheter;
f) an introducer sheath having a proximal end and a distal end, the introducer sheath at least partially radially constricting the stent graft;
g) a distal handle fixed to the proximal end of the introducer sheath, whereby the distal handle and the proximal handle are moveable relative to each other in a longitudinal direction along a longitudinal axis of the stent graft to thereby remove the introducer sheath from the stent graft; and
h) an apex capture assembly that includes,
  i) a distal capture component at the nose cone,
  ii) a proximal capture component defining tines that are mateable with the distal capture component to define a capture opening that releasably captures the proximal apices of the most proximal stent, and
  iii) an apex capture catheter having a proximal end and a distal end, the proximal capture component being fixed to the distal end of the apex capture catheter, the proximal end being releasably fixed to the proximal end of the guidewire catheter, whereby release of the proximal end of the apex capture catheter from the proximal end of the guidewire catheter, and retraction of the apex capture catheter in a proximal direction relative to the guidewire catheter, will separate the proximal capture component from the distal capture component, thereby releasing the proximal apices of the most proximal stent.

3. A method for delivering a fenestrated stent graft to an aneurysm site of a patient, wherein the aneurysm site spans a portion of an artery that includes an arterial branch, comprising the steps of:
a) directing a delivery system to an aneurysm site of a patient, the delivery system includes:
  i) a stent graft having
    1) a luminal graft component defining a fenestration and having a proximal open end, a distal open end, an outside surface and an inside surface, the inside surface defining a lumen extending from the proximal open end to the distal open end, and
    2) a plurality of radially self-expanding stents distributed longitudinally along and fixed to the luminal graft component proximally and distally to the fenestration, and wherein at least one of the luminal graft component and at least a portion of the plurality of radially self-expanding stents define, separately or in combination, openings within the lumen and distributed about the fenestration; and
  ii) a plurality of wires extending longitudinally through the lumen of the luminal graft component and at least one of the proximal open end and the distal open end, at least one of the plurality of wires on each lateral side of the fenestration extending longitudinally through at least one of the openings, whereby the stent graft is selectively constricted by the plurality of wires;
b) aligning the fenestration of the stent graft with a proximal end of an arterial branch;
c) retracting the plurality of wires to release the constricted portion of the stent graft spanning the fenestration, whereby the fenestration is proximate to the proximal end of the arterial branch, thereby delivering the fenestrated stent graft to the aneurysm site of the patient; and
d) delivering a branch prosthesis through the lumen and then through the fenestration, before retracting the plurality of wires from the openings, thereby bridging the fenestration with the arterial branch.

* * * * *